(12) United States Patent
Yamada

(10) Patent No.: US 12,239,420 B2
(45) Date of Patent: Mar. 4, 2025

(54) IMAGE PROCESSING TO DETERMINE LONGITUDINAL ORIENTATION AND GENERATE TOMOGRAPHIC AND LONGITUDINAL VIEWS

(71) Applicant: Canon U.S.A., Inc., Melville, NY (US)

(72) Inventor: Daisuke Yamada, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 156 days.

(21) Appl. No.: 17/064,435

(22) Filed: Oct. 6, 2020

(65) Prior Publication Data

US 2021/0113098 A1  Apr. 22, 2021

Related U.S. Application Data

(60) Provisional application No. 62/915,918, filed on Oct. 16, 2019.

(51) Int. Cl.
*A61B 5/02* (2006.01)
*A61B 5/00* (2006.01)
*A61B 8/08* (2006.01)
*A61B 8/12* (2006.01)
*G06N 20/00* (2019.01)

(52) U.S. Cl.
CPC ........ *A61B 5/02007* (2013.01); *A61B 5/0066* (2013.01); *A61B 5/0071* (2013.01); *A61B 5/0084* (2013.01); *A61B 5/7435* (2013.01); *A61B 5/748* (2013.01); *A61B 8/0841* (2013.01); *A61B 8/085* (2013.01); *A61B 8/0891* (2013.01); *A61B 8/12* (2013.01); *G06N 20/00* (2019.01); *A61B 5/0075* (2013.01)

(58) Field of Classification Search
CPC ....... A61B 8/12; A61B 5/0084; A61B 5/6852; A61B 5/7264; A61B 5/6876; A61B 5/7267
See application file for complete search history.

(56) References Cited

U.S. PATENT DOCUMENTS

| 5,497,776 A | * | 3/1996 | Yamazaki | ............. G01S 15/894 |
| | | | | 600/463 |
| 2012/0075638 A1 | | 3/2012 | Rollins et al. | |
| 2012/0253184 A1 | * | 10/2012 | Furuichi | ................ A61B 5/743 |
| | | | | 600/425 |

(Continued)

FOREIGN PATENT DOCUMENTS

| JP | 2017537768 A | 12/2017 |
| JP | 2018196717 A | 12/2018 |

(Continued)

*Primary Examiner* — Joel Lamprecht
*Assistant Examiner* — Nyrobi Celestine
(74) *Attorney, Agent, or Firm* — Canon U.S.A., Inc. I.P. Division

(57) ABSTRACT

A method for intravascular image processing carries out steps of acquiring intravascular data of a portion of a lumen, determining a region of interest based on characteristics of the acquired data, determining an angle (orientation) for displaying an initial longitudinal view of the portion of the lumen based on the determined region of interest, and displaying the initial longitudinal view based on the determined angle and displaying a tomographic view of the portion of the lumen.

35 Claims, 25 Drawing Sheets

(56) References Cited

U.S. PATENT DOCUMENTS

| | | | | |
|---|---|---|---|---|
| 2014/0046172 A1* | 2/2014 | Kim | | A61B 8/085 600/407 |
| 2014/0098099 A1* | 4/2014 | Welford | | G06T 19/20 345/427 |
| 2014/0100439 A1* | 4/2014 | Jones | | G06T 7/0016 600/407 |
| 2014/0257087 A1* | 9/2014 | Elbasiony | | A61B 5/0066 600/424 |
| 2014/0270430 A1* | 9/2014 | Nair | | A61B 17/22 382/128 |
| 2014/0276020 A1* | 9/2014 | Hutchins | | A61B 8/5261 600/426 |
| 2015/0073279 A1* | 3/2015 | Cai | | A61B 8/5207 600/463 |
| 2015/0087986 A1* | 3/2015 | Nair | | A61B 8/54 600/447 |
| 2015/0088060 A1* | 3/2015 | Wang | | A61M 25/0158 604/95.03 |
| 2015/0112182 A1* | 4/2015 | Sharma | | G06F 18/214 600/408 |
| 2015/0230775 A1* | 8/2015 | Kobayashi | | G06T 3/40 345/629 |
| 2015/0366536 A1* | 12/2015 | Courtney | | A61B 8/445 600/427 |
| 2016/0228089 A1* | 8/2016 | Jamello | | A61B 8/0883 |
| 2017/0103520 A1 | 4/2017 | Gopinath et al. | | |
| 2017/0193658 A1* | 7/2017 | Cardinal | | A61B 8/12 |
| 2020/0129144 A1* | 4/2020 | Rajguru | | A61B 8/463 |
| 2020/0294659 A1* | 9/2020 | Gopinath | | A61B 5/0084 |

FOREIGN PATENT DOCUMENTS

| | | |
|---|---|---|
| WO | 2014/041579 A1 | 3/2014 |
| WO | 2017066108 A1 | 4/2017 |

* cited by examiner

Longitudinal Fluorescence and OCT view

FIG. 14

High NIRAF Signal View

1. En face projection 2D NIRAF image
2. Dark band detection

Interested View

- ☐ Fluorescence View
- ☐ Guidewire Avoidance
- ☐ Lipid
- ☐ Calcification
- ☐ Bifurcation
- ☐ Thin-cap fibroatheroma
- ☐ Edge disection
- ☐ Stent malapposition
- ☐ Stent underexpansion
- ☐ Thrombus

FIG. 23

IMAGE PROCESSING TO DETERMINE LONGITUDINAL ORIENTATION AND GENERATE TOMOGRAPHIC AND LONGITUDINAL VIEWS

CROSS REFERENCE TO RELATED APPLICATIONS

The present application claims the benefit of priority from U.S. Provisional Patent Application No. 62/915,918 filed Oct. 16, 2019, which is hereby incorporated by reference herein in its entirety.

BACKGROUND

Field of the Disclosure

The present disclosure generally relates to image processing and, more particularly, to an image processing apparatus, an image processing method, and a storage medium capable of processing intravascular images and determining longitudinal orientations.

Description of the Related Art

Intravascular imaging is useful to diagnose and/or provide characteristic information of a vascular lumen and can be provided by various imaging modalities including for example, OCT (optical coherence tomography), IVUS (intravascular ultrasound, combinations or hybrids thereof, or the like. Fiber optic catheters and endoscopes have been developed to access internal organs. In cardiology, for example, OCT configurations see structural images of vessels with a catheter. The catheter, which includes a sheath and an optical probe, is navigated to a coronary artery. In order to acquire cross-sectional images of tubes and cavities such as vessels, esophagus and nasal cavities, the optical probe is rotated with a rotary junction, such as an FORJ (fiber optic rotary joint) or the like. The optical probe is simultaneously translated longitudinally during the rotation so that helical scanning pattern images are obtained. This translation is normally performed by pulling the tip of the probe back towards a proximal end and is commonly referred to as a 'pullback'. After the pullback, the acquired data is displayed on a monitor for review. The data may be 3D (three-dimensional) images but typically the display shows 2D (two-dimensional) cross-sectional images.

When 2D images are processed from 3D images, there is a possibility to lose useful information, which users want to see, especially longitudinal 2D views. The 3D view is normally too much information and is not able to display detailed images.

It would be beneficial to overcome these concerns and provide an ability to inhibit information loss during intravascular imaging.

SUMMARY

According to an aspect of the present disclosure, a method for intravascular image processing carries out steps of acquiring intravascular data of a portion of a lumen, determining a region of interest based on the acquired data, determining an angle (orientation) for displaying an initial longitudinal view of the portion of the lumen based on the determined region of interest, and displaying the longitudinal view based on the determined angle and displaying a tomographic view of the portion of the lumen.

According to an aspect of the present disclosure, a method for intravascular image processing carries out steps of acquiring intravascular data of a portion of a lumen, determining an ROI based on characteristics of the acquired data, determining a position in a longitudinal direction for displaying an initial longitudinal view of the portion of the lumen based on the determined ROI, and displaying one or more portions in the longitudinal view based on the determined position and displaying a tomographic view of the portion of the lumen.

According to an aspect of the present disclosure, the characteristics are fluorescence or shadows of the acquired intravascular data. The method further includes processing the intravascular data using artificial intelligence or machine learning. The processing is iterative. The intravascular data is obtained by MMOCT, wherein the MMOCT includes one or more of OCT, IVUS, NIRF, NIRAF, and NIRS. The ROI of the method includes one or more of high fluorescence regions, guidewire, and tissue characteristics, wherein the tissue characteristics include one or more of lipid, calcifications, bifurcation, thin-cap fibroatheroma, edge dissection, stent malapposition, stent underexpansion, thrombus, tissue protrusion, and stenosis.

According to aspects of the present application, the methods further include displaying a button on the display, and in response to a click on the display button, displaying the initial longitudinal view. The initial longitudinal view is a cross-sectional longitudinal view or a three-dimensional half pipe cut longitudinal view. The methods further include presetting a type of the ROI for determining the display angle. In a case there are multiple ROIs, the methods include selecting one of the multiple ROIs, and moving to another ROI with a click on a display button. The methods further include simultaneously displaying the multiple regions. The methods further include displaying the angle on the tomographic view.

According to an aspect of the present disclosure, an apparatus for intravascular image processing includes at least one processor configured to: acquire intravascular data of a portion of a lumen; determine an ROI based on characteristics of the acquired data; determine an angle (orientation) for displaying an initial longitudinal view of the portion of the lumen based on the determined ROI; and display the initial longitudinal view based on the determined angle.

Further features of the present disclosure will become apparent from the following description of exemplary embodiments with reference to the attached drawings.

BRIEF DESCRIPTION OF THE DRAWINGS

FIG. 14 illustrates a longitudinal OCT view according to the present disclosure.

FIG. 23 illustrates GUI buttons to display interested views according to the present disclosure.

DESCRIPTION OF THE EMBODIMENTS

Various exemplary embodiments, features, and aspects of the disclosure will be described with reference to the drawings.

In the following embodiments, configurations are described that functionally implement intravascular MMOCT (multi-modality optical coherence tomography) imaging and other intravascular imaging modalities including, for example, OCT, IVUS, NIRF (near infrared fluorescence), NIRAF (near infrared autofluoresence), NIRS (near infrared spectroscopy), hybrids or combinations thereof. The present disclosure is not limited to any particular configuration.

Hardware Configuration of Image Processing Apparatus

Figure 1:
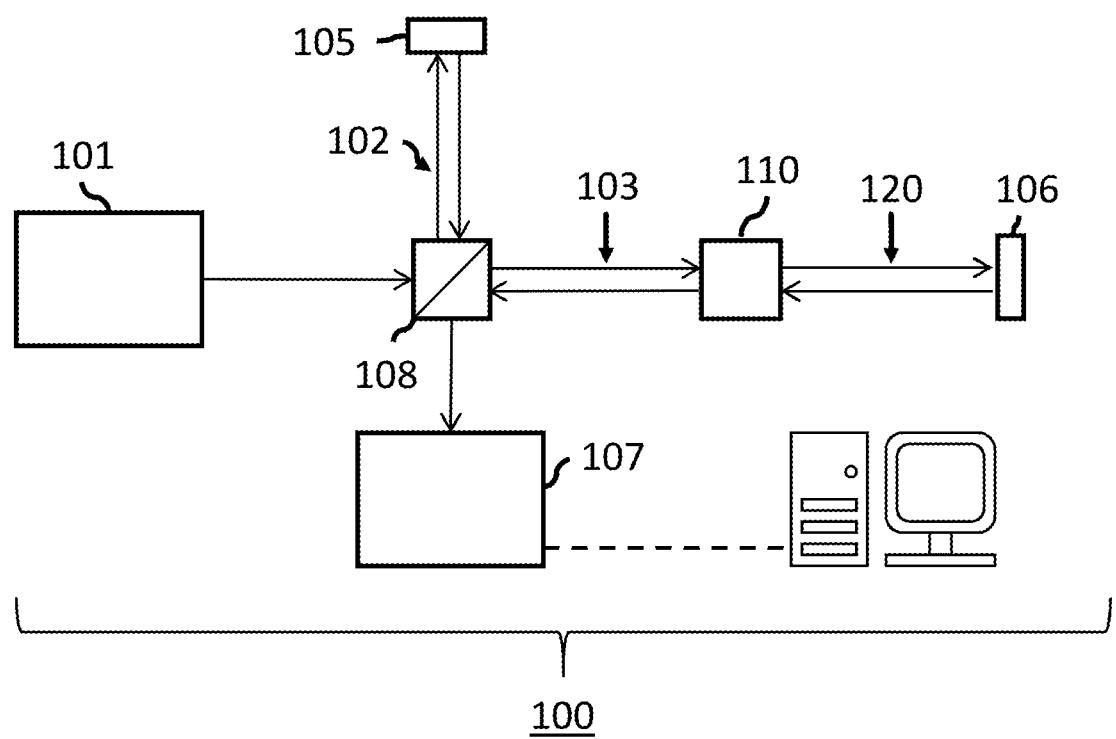
FIG. 1 illustrates a hardware configuration of an image processing apparatus according to an exemplary embodiment of the present disclosure.

FIG. 1 is a block diagram illustrating a hardware configuration of an image processing apparatus 100 according to the present exemplary embodiment.

The image processing apparatus 100 is configured to include one or more of a light source 101, a reference arm 102, a sample arm 103, a reference mirror 105, one or more detectors 107, a deflecting section 108, a PIU (patient interface unit) 110, and a catheter 120. The apparatus 100 includes an interferometer and interacts with a sample 106 via the PIU 110 and/or the catheter 120. The light source produces light to the deflecting section 108, which splits the light from the light source into a reference beam passing into the reference arm 102 and a sample beam passing through the sample arm 103. The deflecting section 108 is positioned at an angle to the reference mirror 105, the one or more detectors and to the sample 106. The reference beam is reflected from the reference mirror 105 in the reference arm 102 while the sample beam is reflected or scattered from a sample 106 through the PIU 110 and the catheter 120 in the sample arm 103. The reference beam and the sample beam combine or recombine at the deflecting section 108 and generate interference patterns. The output of the configuration 100 and/or the interferometer is continuously acquired with the one or more detectors 107, which include one or more photodiodes, multi-array cameras, or the like. Each detector 107 measures interference pattern(s) between the reference arm 102 and the sample arm 103. Electrical analog signals obtained from the output of the configuration 100 and/or the interferometer are converted to digital signals to be analyzed by a computer and output to a display.

The PIU 110 includes one or more of an imaging core spin motor, a linear stage, a fiber optic combiner, a circuit board assembly, control buttons, LEDs (light emitting diodes), or the like. The PIU 110 is configured to provide functions including imaging core rotation, imaging core translation, catheter engage/unlock, user interface, or the like.

The display unit is configured to display images that undergo image processing to generate tomographic 2D views and longitudinal 2D views. 3D OCT views can also be generated for display. A longitudinal view or longitudinal reconstruction of a pullback dataset is obtained at a particular rotational angle. The display unit is configured with a GUI (graphical user interface) to provide one or more buttons for interactive operation. For example, a liquid crystal panel and a backlight module, or an organic EL (electroluminescence) panel can be used for the display unit. The display unit may or may not be detachably attached to the image processing apparatus. The image processing apparatus 100 only needs to have a function of controlling the display by the display unit.

Figure 2:
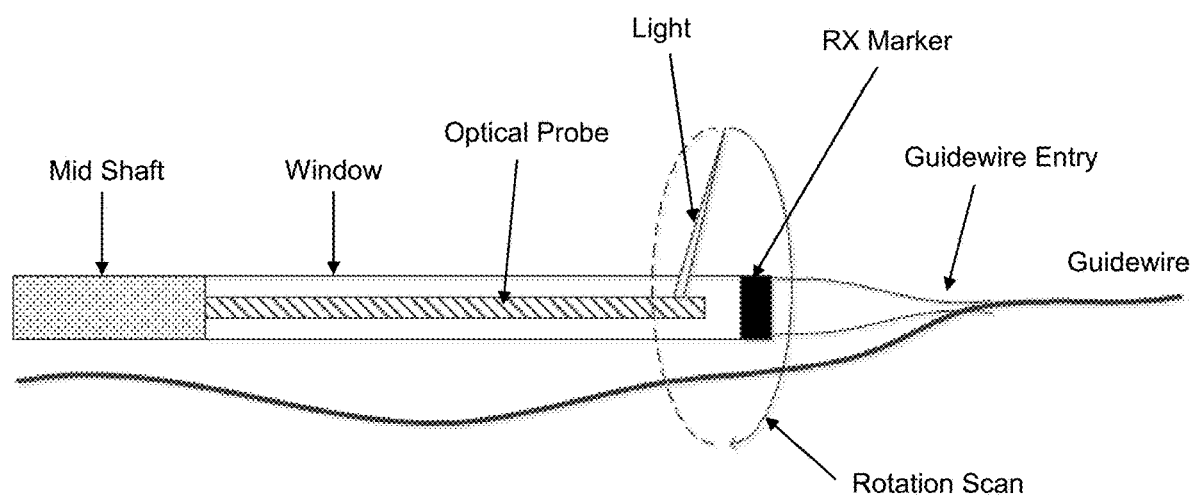
FIG. 2 illustrates a configuration of a catheter according to the present disclosure.

The catheter 120 includes an elongate, flexible, tubular body that is configured for intravascular placement within an internal lumen. As illustrated in FIG. 2, the catheter 120 is configured to rotate for circumferential scanning and includes one or more of a lens, prism or mirror, an optical fiber, an outer casing, an inner sheath, a mid shaft, an optical probe, a light, a gradient index marker, a guidewire, and a guidewire entry, and is configured to rotate for circumferential scanning. The lens is configured as a GRIN (gradient index) lens for focusing. The prism or mirror is for directing light. The inner sheath can be configured as a speedometer cable that carries the optical probe and rotates all but the outer casing. The proximal end has a free space that allows the catheter 120 to rotate while keeping the proximal end fixed.

A drive assembly is removably coupled to the proximal portion of the catheter 120. The drive assembly is configured with a rotary junction that includes an FORJ having a stationary section and a rotatable section. A motor rotates the rotatable section. The shaft of the motor is hollow to allow a portion of the rotatable section of the FORJ to extend therethrough. In a case where the motor is activated, the rotatable section of the FORJ rotates, thereby causing a driveshaft and the optical fiber to rotate.

The FORJ allows an optical signal to be transmitted across an interface between the rotatable section and the stationary section. The FORJ is configured to use optical signals to carry high speed digital data, or analog data with frequency or amplitude sensitive, e.g. analog information. The FORJ is configured to be single or multi-pass and passive or active. A passive FORJ transmits an optical signal from a rotating structure to a stationary structure without any electronic processing although components such as filters and lenses can be used to process the optical signal. An active FORJ incorporates electronics to process a signal to improve rotor to stator transmission properties and can involve electrical/optical conversion, amplification, signal conditioning and re-clocking.

A rotational motor is linked through a belt to the FORJ, which connects the catheter 120 via a connector to translate rotational torque. An optic rotary joint and a brushed electrical slip ring is used for OCT signal coupling to allow the whole probe to rotate freely. These components are fixed to a linear translation stage which functions for imaging pullback.

An ablative element and imaging apparatus are positioned on a proximal segment of the distal tip. The ablative element can be positioned proximal to the imaging apparatus. The ablative element can also be positioned distal to the imaging apparatus. Generally, the catheter is configured to take on any desired profile, application, or the particular tissue of interest.

The catheter 120 scans a focused beam of light circumferentially around the vessel and longitudinally along the vessel using mechanical configurations. The catheter 120 contains a rotating optical fiber that is terminated at its distal end by a lens that focuses the beam and a reflector element, to direct it sideways to the vessel wall. The catheter 120 is connected to a rotary junction where a motor is configured to rotate the optical fiber in the catheter. The rotary junction couples light from the stationary optical fiber at the proximal end to the rotating optical fiber in the catheter. The rotary junction is configured for motorized or automated pullback. Rotation and translation of the fiber in the catheter 120, actuated by the rotary junction and pullback motors, may be transmitted to the distal imaging tip by the optical fiber, or by a flexible drive cable encapsulating the fiber. Optics may be configured within the imaging sheath.

An interface is configured to connect the catheter 120 to the PIU or controller, which includes a GUI. The proximal portion of the catheter 120 includes an elongate body connector that is interconnected with the drive assembly. The drive assembly has a driveshaft that extends through the catheter to rotate an imaging sensor. The drive assembly is configured to rotate the optical fiber and/or the driveshaft. The drive assembly includes an optical fiber or an FORJ to optically connect with the optical fiber of the catheter 120.

The optical fiber has an imaging sensor configured as fiber optic wire that rotates in the catheter 120 and the catheter 120 may be filled with fluid. Imaging is achieved in a case where the fiber optic wire emits light and records the reflection while simultaneously rotating and being pulled back along the artery. The light source 101 uses a bandwidth in the near-infrared spectrum with central wavelengths ranging in a range from around 1250 to 1350 nm. The image is formed by backscattering of light from the vessel wall or the time it takes for emitted light to travel between the target tissue and back to the lens, producing an echo time delay with a measurable signal intensity or magnitude. Multiple axial scans (A-lines) are continuously acquired as the fiber optic wire rotates and a full revolution creates a complete cross section of the vessel. The backscattered signal is measured using an interferometer with a beam splitter in the form of a fiberoptic coupler. The beam splitter splits part of the signal to the tissue and part of the signal to a reference arm including a mirror that moves at calibrated distances to produce echo-delays. The reflected signal from the tissue and from the reference arm are recombined in the beam splitter and an interference measurement is made using, for example, a photodetector. The catheter can be configured in the form of a balloon catheter. Imaging can also be achieved without balloon occlusion. An OCT image is formed by collecting backscattered light from the artery wall and determining the amplitude and the time of flight for the emitted light to travel between the focusing lens and the sample 106 (A-line). Multiple A-lines are acquired by rotating the imaging catheter to create a 2D image (B-scan).

During catheterization, a guidewire is inserted into a vessel through a medical tool, such as a needle or the like, and threaded to a destination, for example, the heart. The needle can be replaced by a sheath that may be a tapered tube. The sheath may be transparent or mostly transparent so that the beam of light can travel through the sheath. The catheter 120 can be hollow and be slid over the guidewire to the target region and then the guidewire can be removed. A second guidewire can be threaded through the catheter and pass through the vessel blockage, where another catheter with a balloon on the end may pass through the guide catheter to the narrowed region. The balloon is inflated with a high pressure to push against the artery wall to relieve the blockage and restore blood flow. The balloon is then deflated and withdrawn together with the catheter, guidewire and sheath. A stent is used to support the narrowed wall and keep the lumen open during the follow up. The guidewire is used to introduce an imaging probe into the lumen. The imaging probe is pulled back along a length of the lumen while collection data. As the probe is retracted through pullback along the vessel, a plurality of scans or data sets are collected as the probe or a portion thereof rotates. These data sets, or collections of frames of image data, can be used to identify ROIs (regions of interest).

ROIs indicate characteristic information, shadowing, or artifacts of imaging that may be affected in a variety of ways including, for example, the guidewire, lumen, side branch, tissue, or the like, and the ROIs include one or more of high fluorescence regions, guidewire, tissue characteristics such as lipid, calcifications, bifurcation, thin-cap fibroatheroma, edge dissection, stent malapposition, stent underexpansion, thrombus, tissue protrusion, stenosis, residual blood, saturation, sew-up, non-uniform rotational distortion, bubble, fold-over, wire eccentricities, or the like. These characteristics are caused through various reasons including, for example, binding of the drive cable or rotating optical components during image acquisition. Imaging irregularities can occur due to friction or defective catheters, a crimped imaging sheath, or the like. Reflections bounce off multiple facets of the catheter 120, which create irregular lines in the image. A blooming effect occurs where excess intensity creates the appearance of a bright reflector that is enlarged and smeared along the axial direction that may occur, for example, along stent strut surfaces. Saturation occurs when a high reflector is encountered by light, where it is backscattered at too high an intensity to be accurately detected by the detector, thereby causing irregularities in affected A-lines. Structures that exhibit high backscattering may include the guidewire, the tissue surface, metallic stent struts, or the like. Saturation irregularities may appear as linear streaks of high and low intensities within the image along the axial direction.

The images generated by the catheter 120 are provided to a display through use of mapping of the OCT signal intensity to a color space that can be displayed on the display. This is achieved through grayscale, e.g. low is black, high is white, or inverted grayscale. The images undergo image processing to generate tomographic 2D views and longitudinal 2D views. 3D OCT views can also be generated. A longitudinal view or longitudinal reconstruction of a pullback dataset can be obtained at a particular rotational angle. The plane through which the longitudinal section is taken intersects the center of mass of the artery or the lumen. Distance measurements can be made using the longitudinal images when the frame rate and pullback speeds are known. Distance measurements in the longitudinal direction are more accurate when obtained through the center of the catheter. Image quality depends on the frame-to-frame spacing, which affects the resolution of the longitudinal imaging along the longitudinal dimension.

3D visualization including cutaway or flythrough views of volume renderings can be utilized to display datasets. These representations encompass multiple frames of a pullback, rather than showing only one cross-sectional image at a time. An overview of the artery wall anatomy is then be provided in an efficient manner. Various parameters affect how these visualization formats appear to the end user including, for example, shading, color maps, segmentation, opacity tables, pitch/frame-to-frame spacing, or the like.

A control section is configured to provide light to, and collect light backscattered from, the vessel through the catheter 120 and the rotary junction. The reflected light signals are detected and converted to digital signals, which are used to generate images. A display is configured to display the images. The control section is configured to control the rotational and pullback speed of the catheter 120. Rotational speed determines both the rate at which individual circular cross-sectional images are obtained and in conjunction with the A-line rate of the configuration, the number of A-lines per image. The pullback speed determines the pitch of the helical scan or frame-to-frame spacing and therefore the spatial resolution along the longitudinal dimension of the image.

Figure 3:
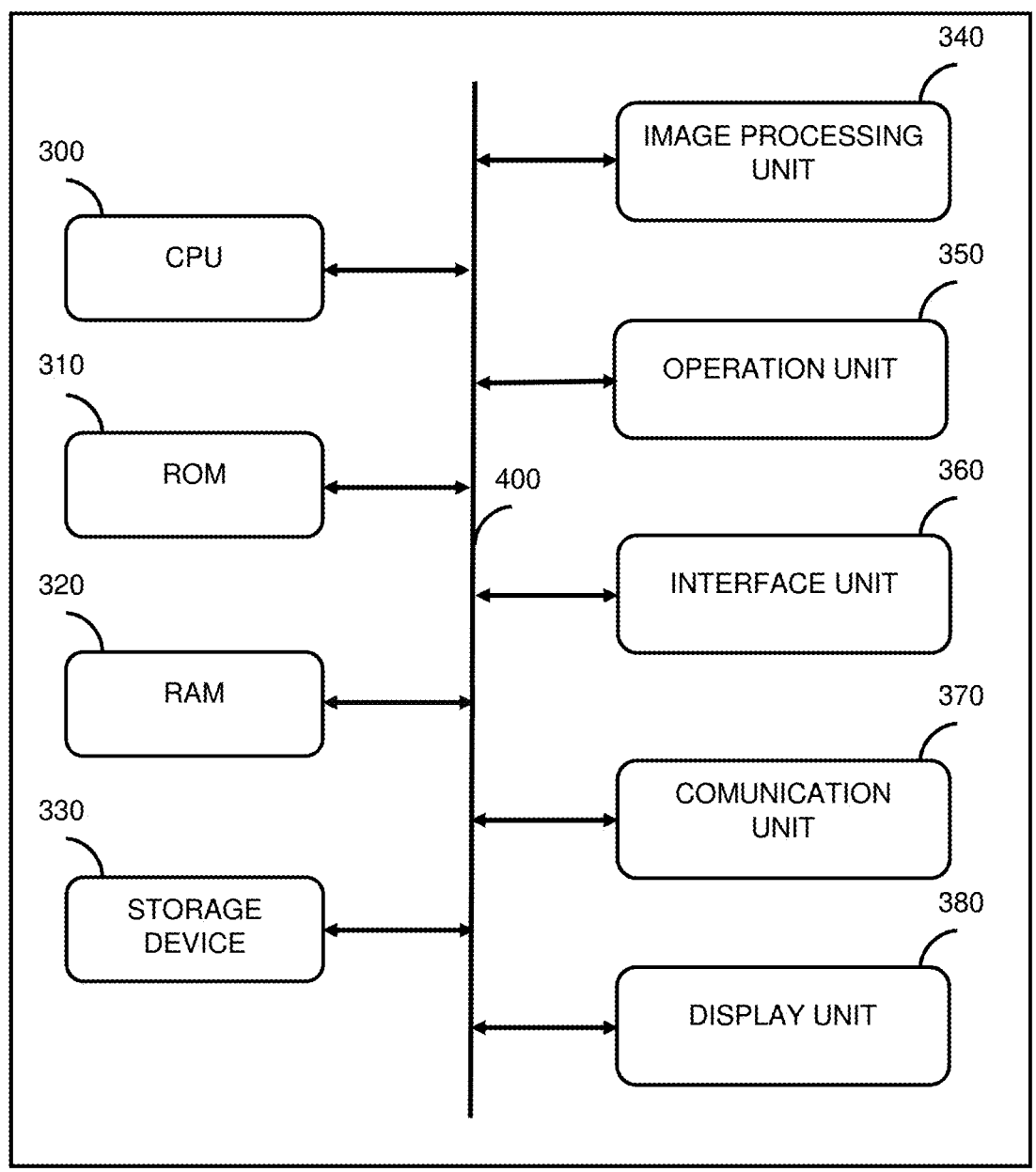
FIG. 3 illustrates a block diagram of the image processing apparatus.

FIG. 3 illustrates a block diagram of the image processing apparatus 100 that includes one or more of a CPU (central processing unit) 300, a ROM (read-only memory) 310, a RAM (random access memory) 320, a storage device 330, an image processing unit 340, an operation unit 350, an interface unit 360, a communication unit 370, and a display unit 380. The CPU 300, which includes one or more processors, one or more memories, circuitry, or a combination thereof, comprehensively controls access to various kinds of devices, which are connected through a system bus 400, in accordance with a control program stored in a ROM 310 or on a storage device 330. An image processing unit 340 processes image data and includes one or more processors, one or more memories, circuitry, or a combination thereof. The ROM 310 stores a control program and the like that are able to be executed by the CPU 300. The RAM 320 functions as a main memory, a work area, and the like of the CPU 300 and is configured to have a memory capacity that is able to be expanded by using an optional RAM connected to an expansion port (not illustrated). The storage device 330 can be configured as an HDD (hard disk drive), an SD (secure digital) card, a flash memory, or the like, that stores a boot program, various kinds of applications, font data, a user file, an edit file, and the like. The storage device can also be configured as an external storage device. The operation unit 350 includes one or more keys, buttons, switches, a mouse, a keyboard, or the like, to perform display control of the display unit 380 and control of input of various kinds of setting information set by an input unit, and to provide inputs to the image processing apparatus 100. The interface unit 360 receives information for imaging control from the image processing apparatus 100. The communication unit 370 facilitates communication into and out of the image processing apparatus 100. The display unit 380 presents a display to a user to view images, data or other information, and can be configured as an LCD (liquid crystal display) or other type of display.

Figure 4:
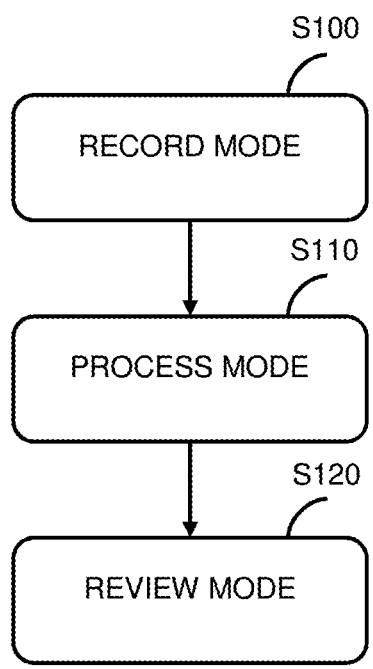
FIG. 4 illustrates intravascular method steps according to the present disclosure.
Figure 5:
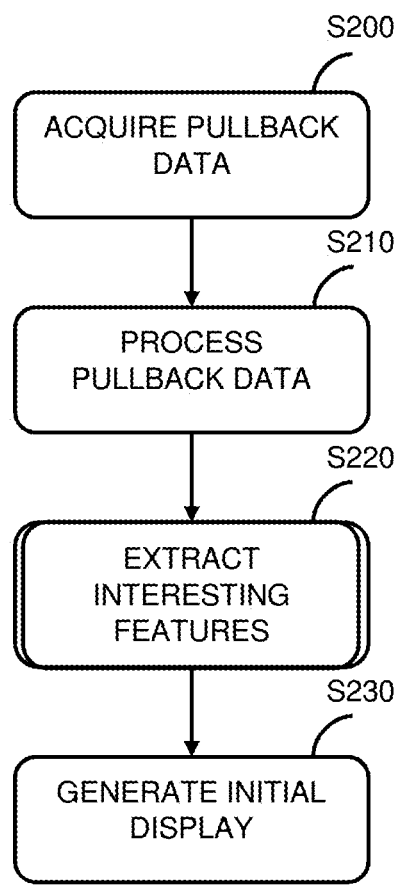
FIG. 5 illustrates intravascular method steps according to the present disclosure.

The acquired pullback data is processed by extracting interesting features to generate an initial display or view of one or more images that are useful or helpful for users, such as doctors, nurses, medical personnel, medical technicians, image researchers, or the like. FIGS. 4 and 5 illustrate general intravascular method steps according to the present disclosure, where FIG. 4 shows a record mode S100, a process mode S110, and a review mode S120. In FIG. 5, pullback data is acquired in S200 by acquiring intravascular data of a portion of a lumen. The data is saved into memory or a hard drive. The acquired pullback data is processed in S210 by MMOCT (multi-modality OCT) signal processing and determining an ROI (region of interest) based on characteristics of the acquired data. An angle (orientation) or a position is determined based on the determined ROI to display an initial longitudinal view of the portion of the lumen. Interesting features are extracted from the ROI in S220. An initial display is generated in S230 to display an initial longitudinal view based on the determined ROI, and display a tomographic view of the portion of the lumen. The present disclosure provides an initial display or view of regions where users want to see without users' manipulations.

The present disclosure provides advantageous features to automatically generate the initial display or view that that is helpful or desirable for the user, such as a doctor or the like, e.g. an optimal initial display image or view, by minimizing processing time needed to generate the initial display. The present disclosure provides processes to determine the best plane to show OCT data.

Figure 6:
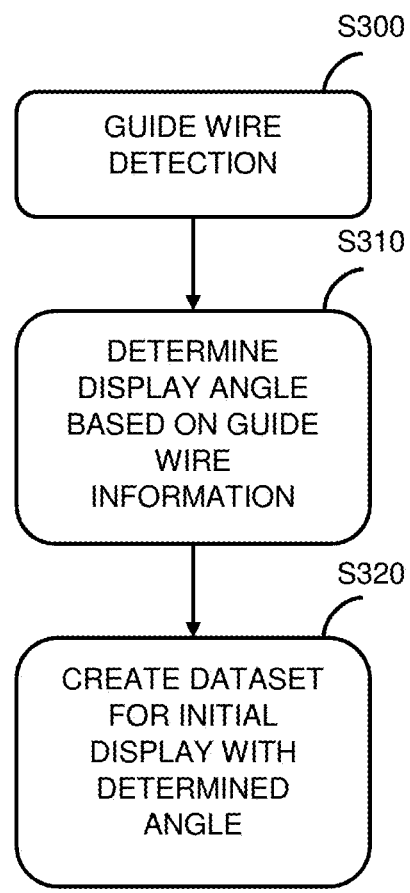
FIG. 6 illustrates intravascular method steps according to the present disclosure.

FIG. 6 illustrates details of the step S220 to extract interesting features according to an embodiment of the present disclosure. Guide wire detection takes place in S300. A display angle is determined based on the guide wire information in S310. A dataset is created for the initial display with a determined angle.

Figure 7:
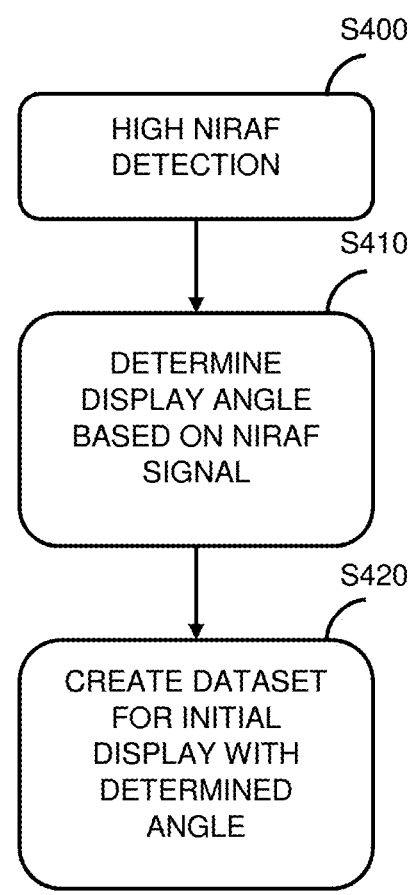
FIG. 7 illustrates intravascular method steps according to the present disclosure.

FIG. 7 illustrates details of the step S220 to extract interesting features according to another embodiment of the present disclosure. High NIRAF detection takes place in S400. A display angle is determined based on the NIRAF signal in S410. A dataset is created for the initial display with a determined angle.

Additional features or aspects of present disclosure can also advantageously implement one or more AI (artificial intelligence) or machine learning algorithms, processes, techniques, or the like, to determine the interesting features described above or otherwise contribute to the generation and display of the initial display image or view to the doctor, operator, or technician. Such AI techniques use a neural network, a random forest algorithm, a cognitive computing system, a rules-based engine, or the like, and are trained based on a set of data to assess types of data and generate output. For example, a training algorithm can be configured to determine the interesting features using one or more models or through analysis of information or datasets retrieved from the pullback data. The model(s) can be configured as software that takes images as input and returns predictions for the given images as output. The model(s) can be an instance of a model architecture (set of parameter values) that has been obtained by model training and selection using a machine learning and/or optimization algorithm/process. A model can generally include, for example, an architecture defined by a source code (e.g. a convolutional neural network including layers of parameterized convolutional kernels and activation functions, or the like) and configuration values (parameters, weights, features, or the like) that are initially set to random values and are then over the course of the training iteratively optimized given data example, an objective function (loss function), an optimization algorithm (optimizer), or the like.

At least some of the pullback data can be used as input data and provided to the training algorithm. Initial data sets can be stored in a database of OCT data, NIRAF data, or the like, that include planes of interest or ROIs that are generated using input mapping to the model(s) or through expert research, and machine learning can find parameters for AI processes. Initial OCT data from the initial data sets are used or placed into an AI process or algorithm to determine ROI for new data. The training algorithm is configured to learn physical relationships in the input data to best describe these relationships or correlations. The data sets include information based on a number of factors including, for example, the acquired medical images, the number of acquired images, the angle of the image, the position of the image, foreign objects in the images, a patient's age, a patient's gender, or the like. The data is evaluated using a weighted evaluation where the weights are learned through a training process, through subject matter specifications, or the like. Deep learning mechanisms can augment an AI process to identify indicators in the image data that can include, for example, imaging abnormalities, the presence of foreign bodies in the image data, or the like.

First Embodiment

Imaging of coronary arteries by MMOCT of an intravascular OCT and fluorescence multi-modality configuration is described in the present embodiment. The configuration of the first embodiment can automatically provide orientation and position of the 2D views based on acquired fluorescence data.

In the MMOCT of the present embodiment, the OCT modality obtains depth resolved structural information while the fluorescence modality obtains molecular information (non-depth resolve) introduced by using excitation beams.

The present embodiment operates through the record mode S100, the process mode S110, and the review mode S120 of FIG. 4.

Figure 8:
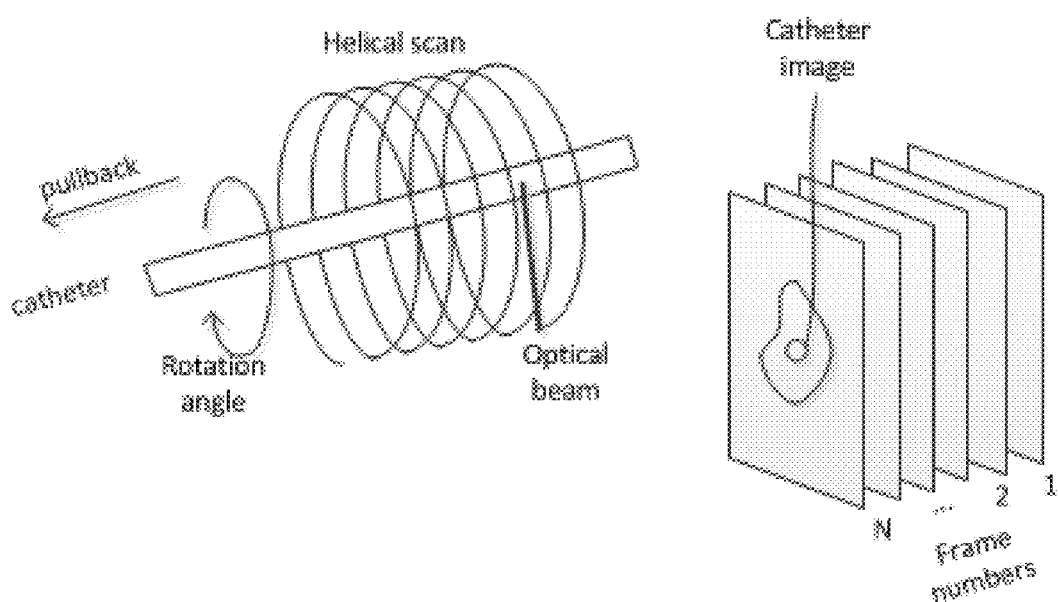
FIG. 8 illustrates optical probe pullback and 2D cross-sectional tomographic frames.

In the record mode S100, 3D OCT and 2D fluorescence synchronized data is acquired using mechanical scanning when the optical probe is simultaneously translated longitudinally (pullback direction) during the rotational spin (rotation direction). Volumetric reconstruction can assume parallel acquisition of 2D cross-sectional tomographic frames with spacing equal to the pitch. FIG. 8 illustrates the optical probe undergoing a helical pullback and sequential parallel reconstruction.

Figure 9:
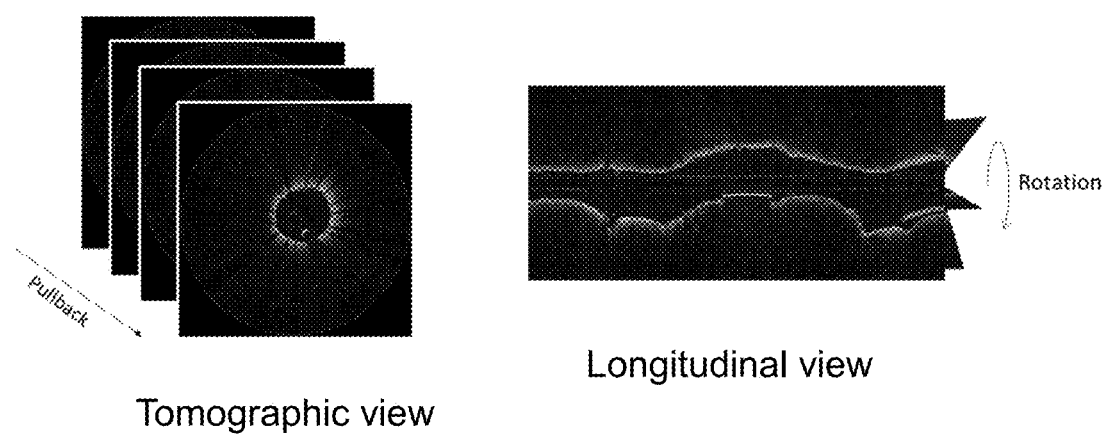
FIG. 9 illustrates OCT data display with a 2D cross-sectional tomographic view (frames), and a longitudinal view according to the present disclosure.
Figure 10:
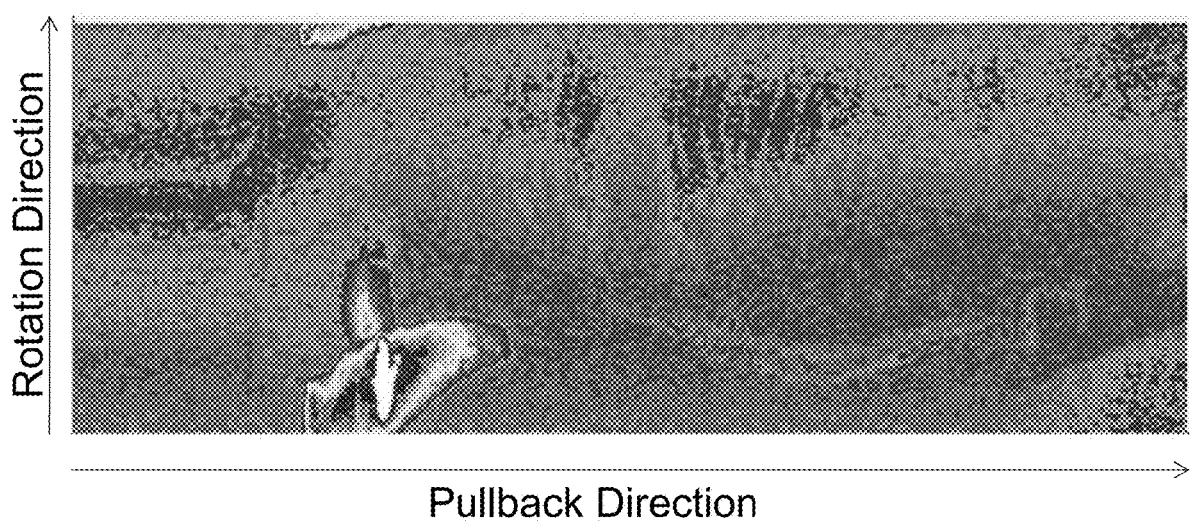
FIG. 10 illustrates a 2D fluorescence carpet view according to the present disclosure.

In the process mode S110, the acquired data is stored in memory. The stored data is subjected to MMOCT signal processing, whereby interesting features are extracted. The interesting features can be In the review mode S120, the OCT data is displayed with a 2D cross-sectional tomographic view (frames) that is the cross sectional plane of perpendicular to pullback (vessel) direction, and/or a longitudinal view that is the cross sectional plane along to the pullback (vessel) direction, as shown in FIG. 9. The fluorescence data can be displayed with a carpet view, which can be expanded with pullback and rotation directions, as shown in FIG. 10. Higher fluorescence signals represent high-risk plaques such as necrotic core compared with normal tissues. The multi-modality system determines the orientation and position where fluorescence signals are elevated, and then displays the 2D cross-sectional tomographic view and the longitudinal view on a display via a GUI with determined orientation and position.

ROIs are searched by calculating a maximum fluorescence value from the acquired 2D fluorescence signals. Before searching the maximum fluorescence value, low-pass filters and/or smoothing techniques can be applied in order to eliminate noise. Then, the frame number (position) and the orientation can be saved. ROIs can also be searched by calculating a center of a maximum size of fluorescence regions. The fluorescence regions are determined as a fluorescence value with greater than a predetermined threshold value. The center is calculated as an average of a position and orientation or fluorescence value weighted position and orientation. ROIs can also be searched by calculation of a maximum or a center of a maximum size from outside the stent region.

ROIs indicate characteristic information of imaging that may be affected in a variety of ways including, for example the guidewire, lumen, side branches, tissue, or the like. The ROIs include one or more of high fluorescence regions, guidewire, tissue characteristics such as lipid, calcifications, bifurcation, thin-cap fibroatheroma, edge dissection, stent malapposition, stent underexpansion, thrombus, tissue protrusion, stenosis, residual blood, saturation, sew-up, non-uniform rotational distortion, bubble, fold-over, wire eccentricities, or the like.

Figure 11A:
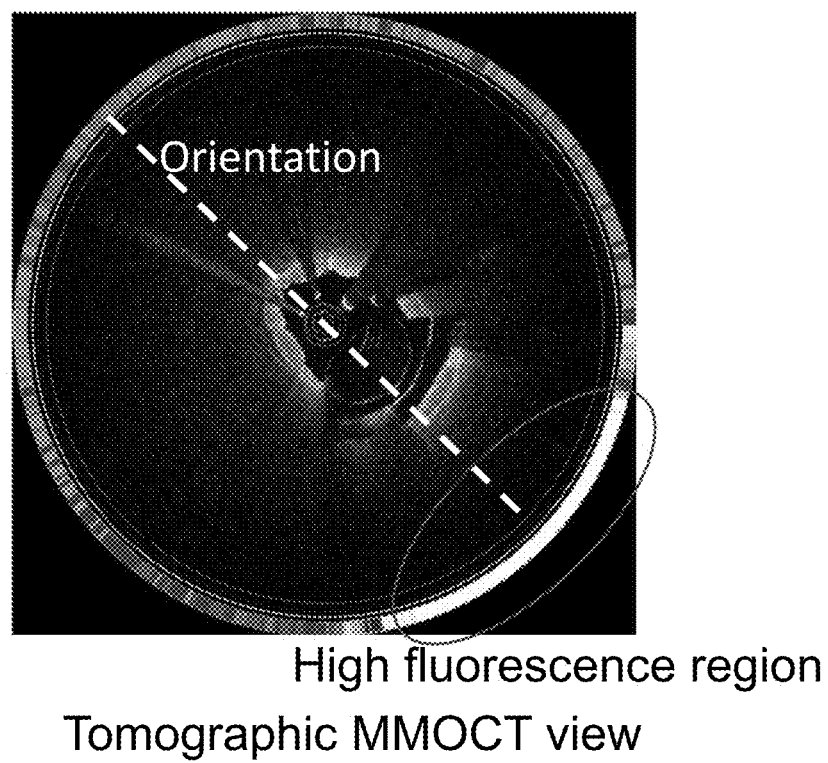
FIG. 11A illustrates a tomographic MMOCT view according to the present disclosure.
Figure 11B:
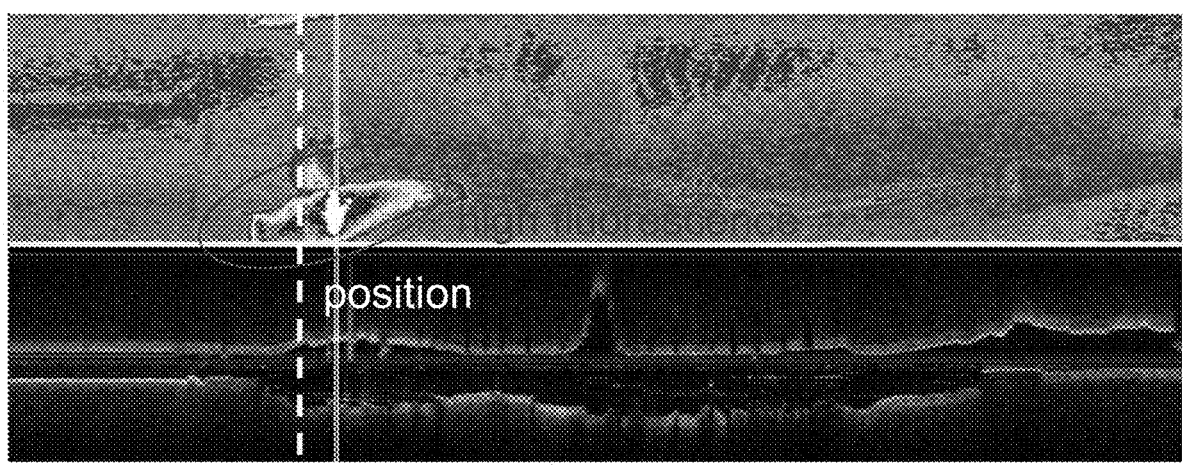
FIG. 11B illustrates a longitudinal fluorescence and OCT view according to the present disclosure.

FIGS. 11A and 11B illustrate the tomographic MMOCT view and the longitudinal view of OCT and fluorescence. In displaying ROIs, the position (frame) of the tomographic view and the orientation of the longitudinal view are determined with predetermined ROIs where the fluorescence signals are elevated. Both OCT and fluorescence images near high fluorescence regions are viewable on the display without manipulations by a user.

In a first example, after the pullback acquisition, the OCT configuration automatically displays determined views at ROI initial views so users are able to see ROIs in a first or initial view without any operations.

In a second example, a button is displayed by the GUI to redisplay elevated fluorescence regions. The button provides a user friendly feature to avoid manipulations/inputs by the user which involve multiple operations so that users are able to save time.

In the present embodiment, the pullback data is recorded. A trigger signal can be used to trigger a single depth scan on an A/D (analog to digital) converter, and record a value of a digital counter, and a digital counter can receive a rotary motor encoder signal and pullback motor encoder signal, respectively. The encoder signals can be TTL pulse trains which switch at a defined rate per motor revolution. By counting these switches using digital counters, the current motor positions can be measured. The A/D converter and digital counters are contained in the data acquisition unit. The beam is rotated and displaced axially to create a spiral imaging pattern. Scanning occurs with a combination of axial scanning and rotational scanning, where axial scanning occurs, followed by rotational scanning, or rotational scanning occurs, followed by axial scanning. The data is saved into memory and/or a hard drive. The data is subject to signal processing, where adjustment of the angle causes guidewire artifacts to be removed from the imagery. Guidewire artifacts are extracted from the image through the following steps. Guidewire detection takes place and the display angle is determined based on the guidewire information. A dataset is created for initial display with the determined angle. The processed image is displayed on a display, and can be viewed with a manipulated angle.

In the first embodiment, an ROI is determined based on OCT data, NIRAF data, or the like, a defect region (shadow) can be determined, and an angle/orientation can be determined.

In a case where an ROI is determined based on OCT data, the ROI is determined based on the tissue types analyzed with the OCT signal characteristics such as one or more of an attenuation coefficient (scattering and absorption of the tissue characteristic), speckle size, the tissue layer thickness layer, or the like. The tissue types could be lipid, necrotic core, calcium, TCFA (thin-cap fibrousatheroma), or the like.

In a case where an ROI is determined based on NIRAF data, the ROI is determined based on the high NIRAF region. The NIRAF signal indicates the presence of high-risk plaques and/or thrombosis. A neighborhood average can be calculated to introduce the NIRAF region so that the NIRAF region also indicates the size of the plaque (plaque burden) or thrombosis. Also, the NIRAF region could be the highest NIRAF data in the pullback so that the ROI reflects the highest progressive region.

A defect region (shadow) is determined based on the guidewire shadow. The guidewire is used to navigate the MMOCT catheter to the coronary artery, however, the guidewire is made of non-transparent material, so the OCT and NIRAF images become shadows where the guidewire exists. The guidewire can be analyzed and detected by using the OCT data (the tissue surface (lumen) continuity, shadow area, strong reflection from the guidewire, etc.).

An angle/orientation is determined to display the ROI. The angle/orientation is calculated to select the center of the ROI. Also, the angle/orientation is determined to hide the defect regions. The angle/orientation is calculated to display off-angle of the defect regions such as plus or minus 90 degrees so that the system is able to display non-defect regions. The angle/orientation can be considered to use the multiple ROIs and the defect regions. The ROIs and defect regions are weighted based on the user's preference.

The following is a method for intravascular image processing according to the first embodiment. The method carries out steps of acquiring intravascular data of a portion of a lumen, determining an ROI based on characteristics of the acquired data, determining an angle (orientation) for displaying an initial longitudinal view of the portion of the lumen based on the determined ROI, and displaying the initial longitudinal view based on the determined angle and displaying a tomographic view of the portion of the lumen.

The following is another method for intravascular image processing according to the first embodiment. The method carries out steps of acquiring intravascular data of a portion of a lumen, determining an ROI based on characteristics of the acquired data, determining a position in a longitudinal direction for displaying an initial longitudinal view of the portion of the lumen based on the determined ROI, and displaying one or more portions in the longitudinal view based on the determined position and displaying a tomographic view of the portion of the lumen.

The characteristics are fluorescence or shadows of the acquired intravascular data. The method further includes processing the intravascular data using artificial intelligence or machine learning. The processing is iterative. The intravascular data is obtained by MMOCT, wherein the MMOCT includes one or more of OCT, IVUS, NIRF, NIRAF, and NIRS. The ROI of the method includes one or more of high fluorescence regions, guidewire, and tissue characteristics, wherein the tissue characteristics include one or more of lipid, calcifications, bifurcation, thin-cap fibroatheroma, edge dissection, stent malapposition, stent underexpansion, thrombus, tissue protrusion, and stenosis.

The methods according to the first embodiment further include displaying a button on the display, and in response to a click on the display button, displaying the initial longitudinal view. The initial longitudinal view is a cross-sectional longitudinal view or a three-dimensional half pipe cut longitudinal view. The methods according to the first embodiment further include presetting a type of the ROI for determining the display angle. In a case there are multiple ROIs, the methods include selecting one of the multiple ROIs, and moving to another ROI with a click on a display button. The methods according to the first embodiment further include simultaneously displaying the multiple regions. The methods further include displaying the angle on the tomographic view.

The following is an apparatus for intravascular image processing according to the first embodiment. The intravascular image processing apparatus includes at least one processor configured to: acquire intravascular data of a portion of a lumen; determine an ROI (region of interest) based on characteristics of the acquired data; determine an angle (orientation) for displaying an initial longitudinal view of the portion of the lumen based on the determined ROI; and display the initial longitudinal view based on the determined angle.

Second Embodiment

Figure 14:
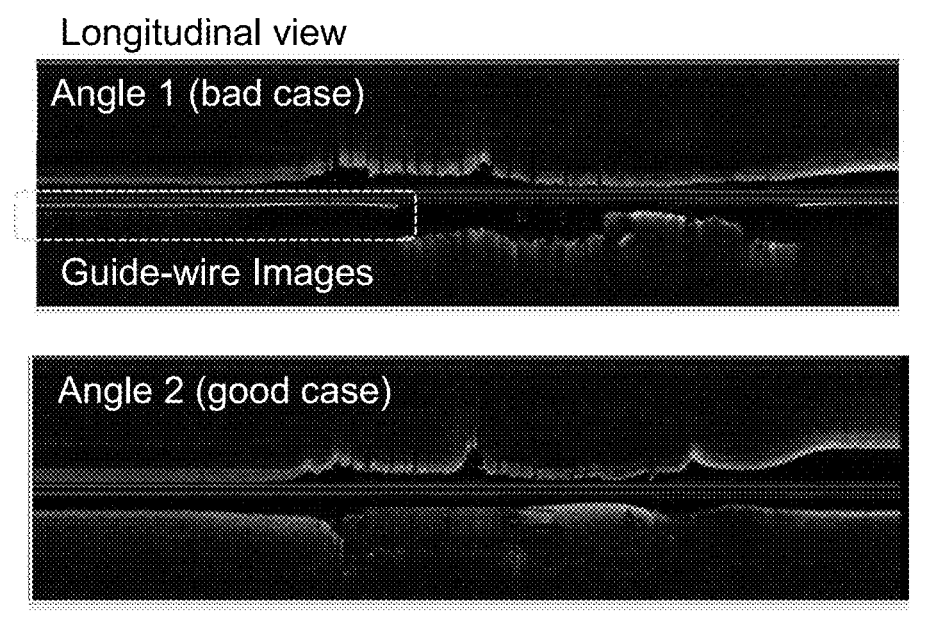

In the MMOCT of the present embodiment, the pullback data is recorded. The data is saved into memory and/or a hard drive. The data is subject to signal processing, where guidewire artifacts are removed from the imagery. Guidewire artifacts are extracted from the image through the following steps. High NIRAF detection takes place. The display angle is determined based on the high NIRAF signal, as shown in FIG. 14. A dataset is created for initial display with the determined angle. The processed image is displayed on a display, and can be viewed with a manipulated angle.

Imaging of coronary arteries by intravascular OCT configuration is described in the first embodiment. In particular, the first configuration displays longitudinal 2D OCT views without guidewire shadows.

In the second embodiment, a guidewire is implemented in the catheter 120 into an ROI in a coronary artery. The coronary imaging catheter has a guidewire entry at the distal part to pass through the guidewire.

Figure 12:
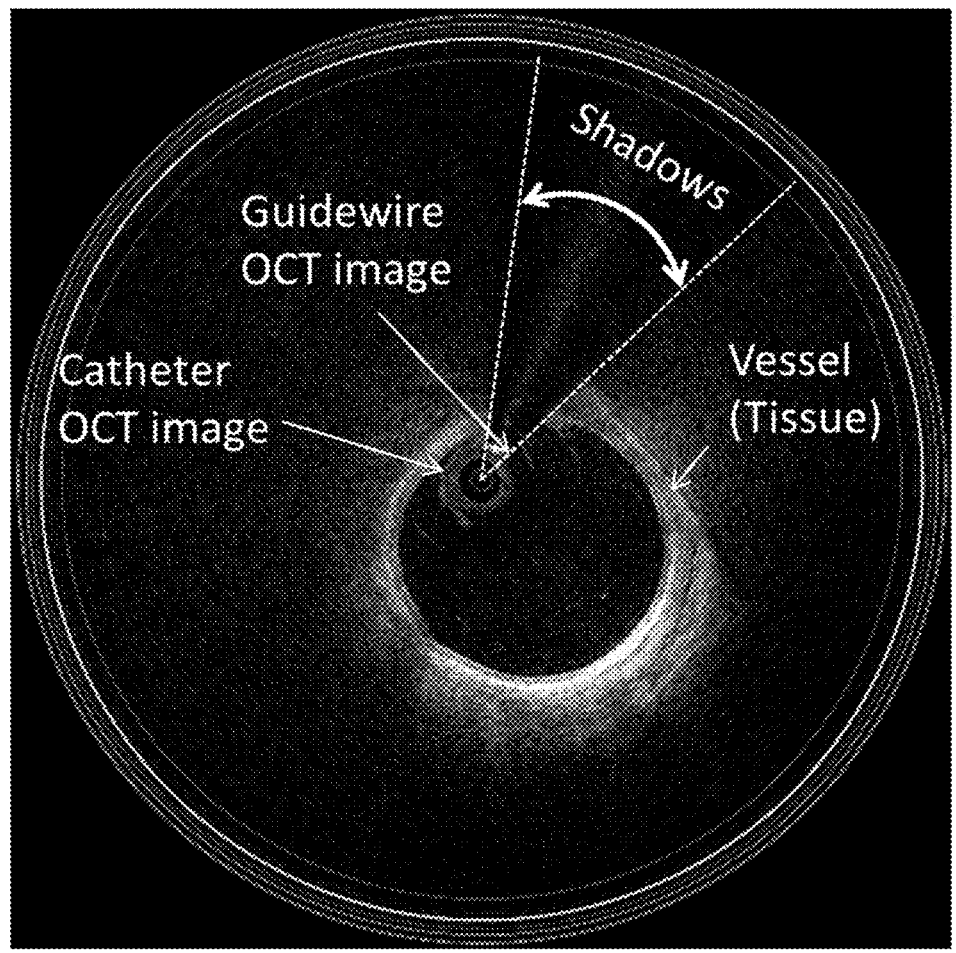
FIG. 12 illustrates a coronary artery OCT view according to the present disclosure.

The OCT catheter images are acquired in a case where the optical probe inside the catheter sheath is simultaneously translated longitudinally (pullback direction) during the rotational spin (rotation direction). However, the light from the catheter can be blocked at the guidewire and not be able to transmit to tissues so that the guidewire generates shadows (or artifacts), as shown in FIG. 12. Therefore, the OCT longitudinal view without the shadows is desirable to prevent the imagery being misleading.

Figure 13:
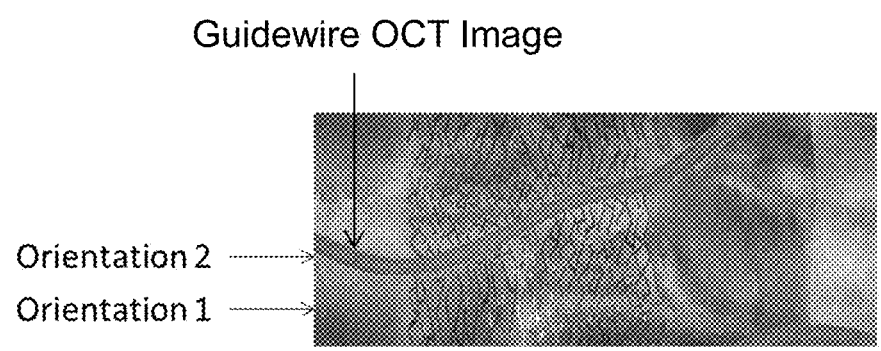
FIG. 13 illustrates an OCT carpet view according to the present disclosure.

Once 3D OCT images are generated, the guidewire is detected with image processing techniques. One example to detect a guidewire occurs when a carpet OCT image with pullback and rotation directions is calculated to integrate the OCT depth (A-line) directions. The guidewire OCT image is segmented with an edge detection technique, as shown in FIG. 13.

The orientations of the guidewire as a function of frame numbers (or pullback direction) are calculated and saved. The guidewire orientation is calculated to avoid guidewire orientation.

The calculations can include: (1) determining a constant orientation with a single frame; (2) determining a constant orientation with several frames to minimize shadows; and (3) determining varied orientations as a function of pullback directions to trace twisted guidewire shadows.

Figure 15:
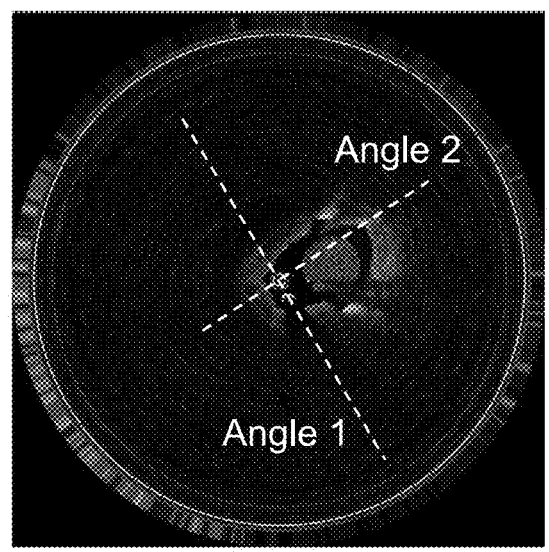
FIG. 15 illustrates a tomographic OCT view according to the present disclosure.

An orientation at a good angle provides a display where no guidewire image appears in the OCT longitudinal view, as shown in FIG. 14. An orientation at a bad angle (angle 1) can provide a display where the guidewire shadows (artifacts) appear and can result in misleading measurements of lumen size. An orientation at a good angle (angle 2) is shown where there are also no tissue images due to the shadows so that users may miss ROIs regarding tissue characterizations. The display view according to the second embodiment is able to prevent misleading users and avoid guidewire shadows and artifacts. A tomographic view comparing angles generally characterized as good or bad is shown in FIG. 15, where angle 1 may be considered a bad angle and angle 2 may be considered a good angle.

In a first example of the second embodiment, after the pullback acquisition, the second embodiment configuration may automatically display determined views at ROIs as initial views so users are able to avoid guidewire artifacts in a first view without any operations.

In a second example of the second embodiment, the GUI provides a button on the display in the review process to redisplay the longitudinal view at an angle that avoids guidewire artifacts. The button is a user friendly feature to avoid manipulations/inputs by a user which may involve multiple operations so that users are able to save time.

Figure 16:
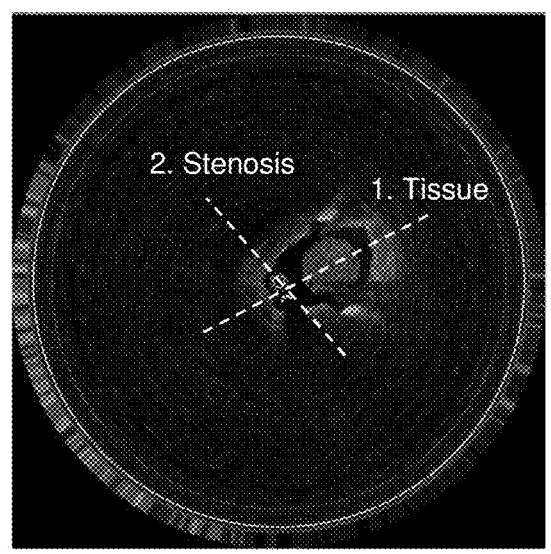
FIG. 16 illustrates OCT variations according to the present disclosure.

Variations other than guidewire, such as stenosis and tissue are shown in FIG. 16. Tissue characterization may include calcification, lipid, TCFA, or the like, and bifurcation may occur.

In the second embodiment, an ROI can be determined based on OCT data, NIRAF data, or the like, a defect region (shadow) can be determined, and an angle/orientation can be determined.

In a case where an ROI is determined based on OCT data, the ROI is determined based on the tissue types analyzed with the OCT signal characteristics such as one or more of an attenuation coefficient (scattering and absorption of the tissue characteristic), speckle size, the tissue layer thickness layer, or the like. The tissue types could be lipid, necrotic core, calcium, TCFA, or the like.

In a case where an ROI is determined based on NIRAF data, the ROI is determined based on the high NIRAF region. The NIRAF signal indicates the presence of high-risk plaques and/or thrombosis. A neighborhood average can be calculated to introduce the NIRAF region so that the NIRAF region also indicates the size of the plaque (plaque burden) or thrombosis. Also, the NIRAF region could be the highest NIRAF data in the pullback so that the ROI reflects the highest progressive region.

A defect region (shadow) is determined based on the guidewire shadow. The guidewire is used to navigate the MMOCT catheter to the coronary artery, however, the guidewire is made of non-transparent material, so the OCT and NIRAF images become shadows where the guidewire exists. The guidewire can be analyzed and detected by using the OCT data (the tissue surface (lumen) continuity, shadow area, strong reflection from the guidewire, etc.).

The following is an intravascular image processing method according to the second embodiment. The method carries out steps of acquiring intravascular data of a portion of a lumen, determining an ROI based on characteristics of the acquired data, determining an angle (orientation) for displaying an initial longitudinal view of the portion of the lumen based on the determined ROI, and displaying the initial longitudinal view based on the determined angle and displaying a tomographic view of the portion of the lumen.

The following is another method for intravascular image processing according to the second embodiment. The method carries out steps of acquiring intravascular data of a portion of a lumen, determining an ROI based on characteristics of the acquired data, determining a position in a longitudinal direction for displaying an initial longitudinal view of the portion of the lumen based on the determined ROI, and displaying one or more portions in the longitudinal view based on the determined position and displaying a tomographic view of the portion of the lumen.

Third Embodiment

In the MMOCT of the present embodiment, the pullback data is recorded. The data is saved into memory and/or a hard drive. The data is subject to signal processing, where guidewire artifacts are removed from the imagery. Guidewire artifacts are extracted from the image through the following steps. Guidewire detection takes place, the display angle is determined based on the guidewire information. A dataset is created for initial display with the determined angle. The processed image is displayed on a display, and can be viewed with a manipulated angle.

Imaging of coronary arteries by intravascular OCT configuration is described in the first embodiment. In particular, the first configuration displays longitudinal 2D OCT views without guidewire shadows.

In the third embodiment, process workflow provides initial display based on acquired data.

In the record mode, the configuration of the third embodiment acquires 3D data with mechanical scanning.

In the process mode, the configuration of the third embodiment saves the data, signal processes the data to reconstruct images, and extracts artifacts where the configuration searches the ROIs and determines the positions (frames) and orientations to display.

In the review mode of the third embodiment, the configuration of the third embodiment provides initial display view with predetermined position and orientation in process mode. The third embodiment configuration also allows users to analyze and manipulate images with inputs of the users.

Figure 17:
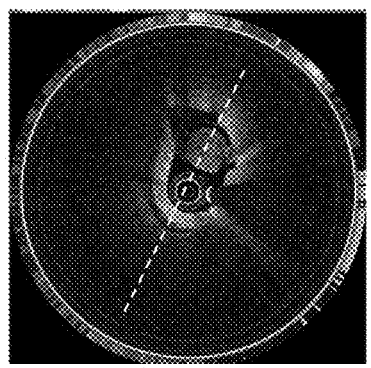
FIG. 17 illustrates a high NIRAF signal view according to the present disclosure.
Figure 17:
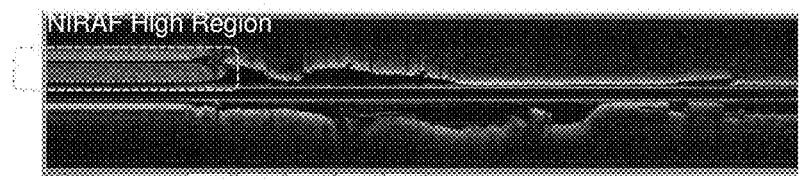
Figure 18:
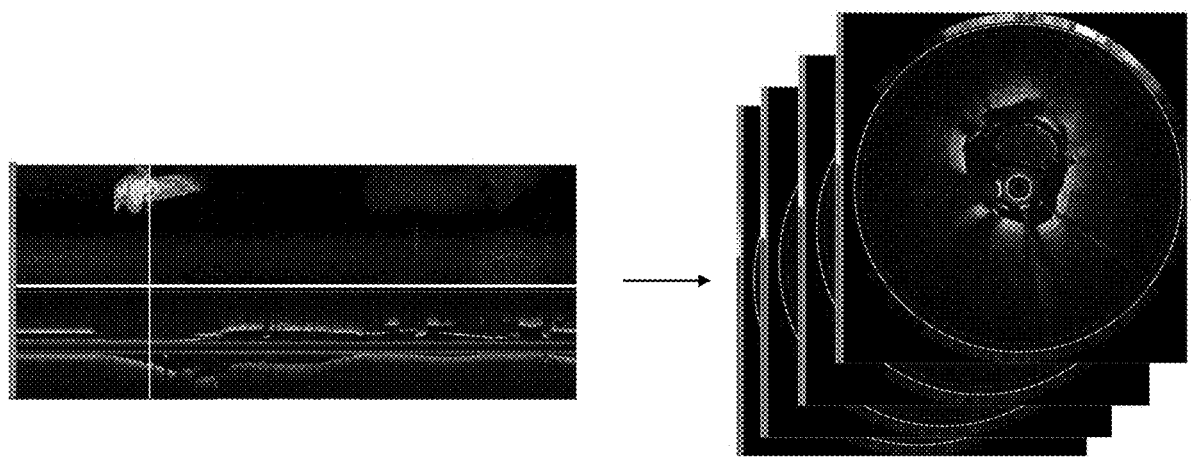
FIG. 18 illustrates tomographic frame numbers according to the present disclosure.
Figure 19:
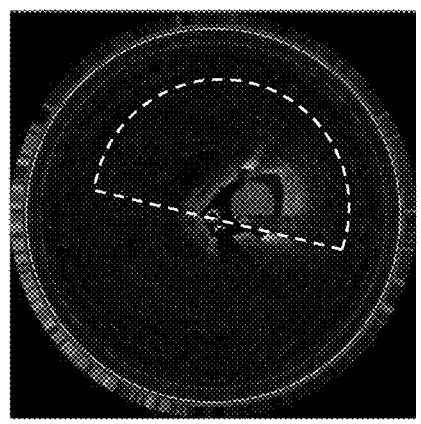
FIG. 19 illustrates a half 3D longitudinal view according to the present disclosure.
Figure 20:
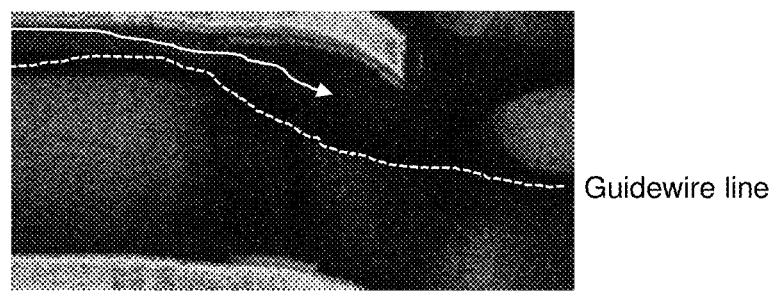
FIG. 20 illustrates an NIRAF signal when a guidewire is twisted, or an NIRAF signal is twisted according to the present disclosure.
Figure 21:
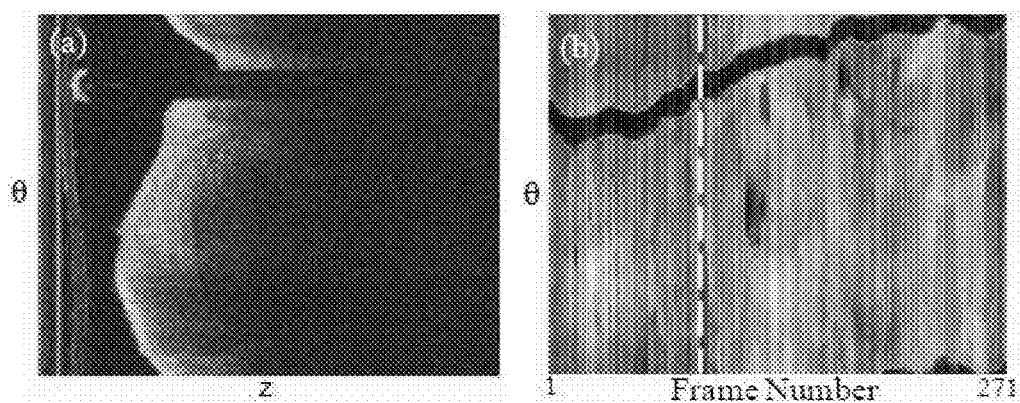
FIG. 21 illustrates an example of guidewire detection according to the present disclosure.
Figure 22:
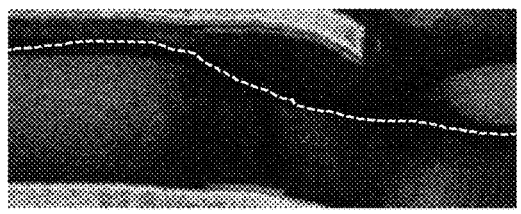
FIG. 22 illustrates an example of guidewire detection according to the present disclosure.

FIG. 17 shows a high NIRAF signal view. FIG. 18 shows tomographic frame numbers. FIG. 19 shows a half 3D longitudinal view. FIG. 20 illustrates an NIRAF signal when a guidewire is twisted, or the NIRAF signal is twisted. The longitudinal view is determined with a predetermined region (center of pullback), and the average of the trace lines. The longitudinal view is continually oriented along the guidewire or NIRAF signal trace lines. FIGS. 21 and 22 illustrate examples of guidewire detection.

In the third embodiment, an ROI can be determined based on OCT data, NIRAF data, or the like, a defect region (shadow) can be determined, and an angle/orientation can be determined.

In a case where an ROI is determined based on OCT data, the ROI is determined based on the tissue types analyzed with the OCT signal characteristics such as one or more of an attenuation coefficient (scattering and absorption of the tissue characteristic), speckle size, the tissue layer thickness layer, or the like. The tissue types could be lipid, necrotic core, calcium, TCFA, or the like.

In a case where an ROI is determined based on NIRAF data, the ROI is determined based on the high NIRAF region. The NIRAF signal indicates the presence of high-risk plaques and/or thrombosis. A neighborhood average can be calculated to introduce the NIRAF region so that the NIRAF region also indicates the size of the plaque (plaque burden) or thrombosis. Also, the NIRAF region could be the highest NIRAF data in the pullback so that the ROI reflects the highest progressive region.

A defect region (shadow) is determined based on the guidewire shadow. The guidewire is used to navigate the MMOCT catheter to the coronary artery, however, the guidewire is made of non-transparent material, so the OCT and NIRAF images become shadows where the guidewire exists. The guidewire can be analyzed and detected by using the OCT data (the tissue surface (lumen) continuity, shadow area, strong reflection from the guidewire, etc.).

The following is an intravascular image processing according to the third embodiment. The method carries out steps of acquiring intravascular data of a portion of a lumen, determining an ROI based on characteristics of the acquired data, determining frame for displaying an initial longitudinal view of the portion of the lumen based on the determined ROI, and displaying the initial longitudinal view based on the determined frame and displaying a cross-sectional tomographic view of the portion of the lumen based on the determined frame in at least a tomographic view and a longitudinal view.

The following is another method for intravascular image processing according to the third embodiment. The method carries out steps of acquiring intravascular data of a portion of a lumen, determining an ROI based on characteristics of the acquired data, determining a position in a longitudinal direction for displaying an initial longitudinal view of the portion of the lumen based on the determined ROI, and displaying one or more portions in the longitudinal view based on the determined position and displaying a tomographic view of the portion of the lumen.

Fourth Embodiment

In the MMOCT of the present embodiment, the pullback data is recorded and saved into memory and/or a hard drive. The data is subject to signal processing, where guidewire artifacts are removed from the imagery. Guidewire artifacts are extracted from the image through the following steps. Guidewire detection takes place, the display angle is determined based on the guidewire information. A dataset is created for initial display with the determined angle. The processed image is displayed on a display, and can be viewed with a manipulated angle.

Imaging of coronary arteries by intravascular OCT configuration is described in the first embodiment. In particular, the first configuration displays longitudinal 2D OCT views without guidewire shadows.

In the present embodiment, the review mode is described. The GUI provides buttons to display ROIs on the display, as shown in FIG. 23.

ROIs indicate characteristic information of imaging that are affected in a variety of ways including, for example, the guidewire, lumen, side branches, tissue, or the like, and the ROIs include one or more of high fluorescence regions, guidewire, tissue characteristics such as lipid, calcifications, bifurcation, thin-cap fibroatheroma, edge dissection, stent malapposition, stent underexpansion, thrombus, tissue protrusion, and stenosis, residual blood, saturation, sew-up, non-uniform rotational distortion, bubble, fold-over, wire eccentricities, or the like.

In the fluorescence view, the configuration of the fourth embodiment displays high fluorescence regions with tomographic and longitudinal views, as described above.

The configuration of the fourth embodiment displays tomographic and longitudinal views without guidewire shadows, as described above in the second embodiment.

Figure 24:
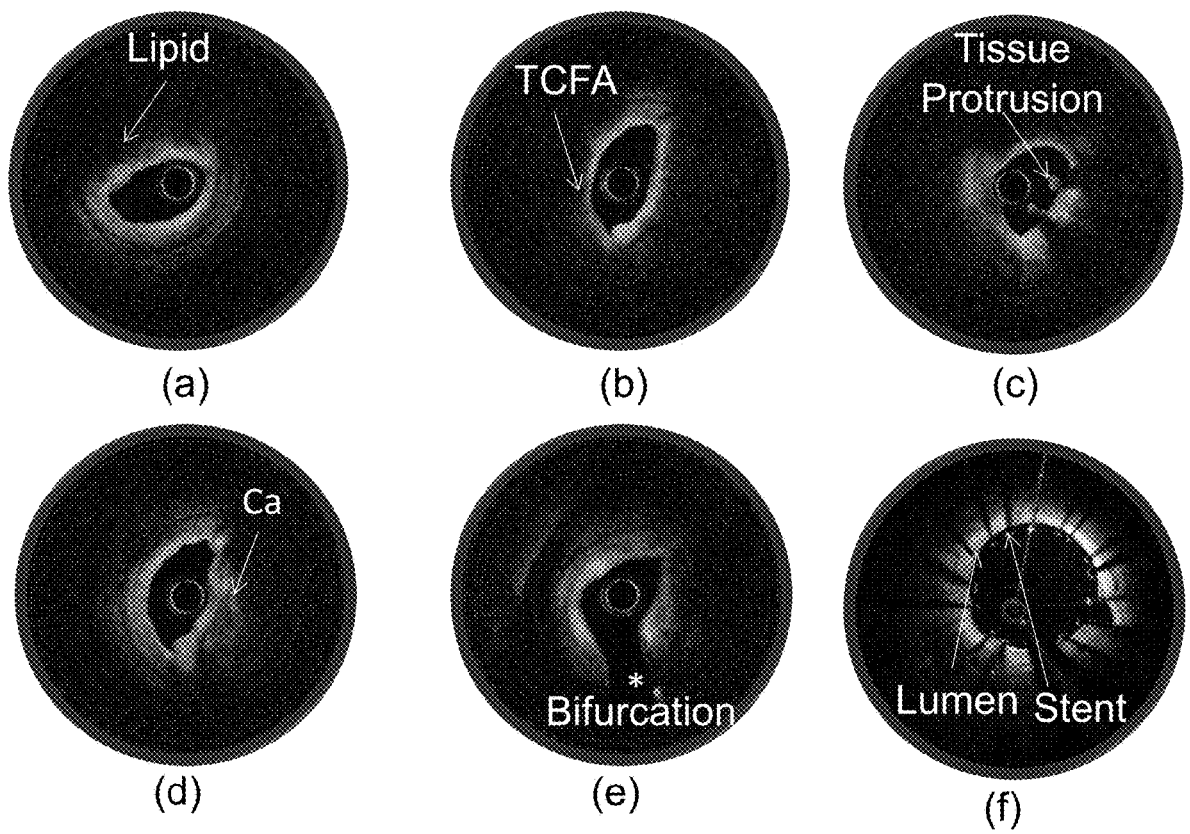
FIG. 24 illustrates tissue characteristic tomographic views according to the present disclosure.

The configuration of the fourth embodiment displays tomographic and/or longitudinal views with selected tissue characteristics in a case where a user selects interested views. FIG. 24 illustrates examples of tomographic views with different tissue characteristics including (a) lipid, (b) TCFA (thin-cap fibroatheroma), (c) tissue protrusion, (d) calcification, (e) bifurcation, and (f) stent malapposition and/or underexpansion.

In the fourth embodiment, an ROI can be determined based on OCT data, NIRAF data, or the like, a defect region (shadow) can be determined, and an angle/orientation can be determined.

In a case where an ROI is determined based on OCT data, the ROI is determined based on the tissue types analyzed with the OCT signal characteristics such as one or more of an attenuation coefficient (scattering and absorption of the tissue characteristic), speckle size, the tissue layer thickness layer, or the like. The tissue types could be lipid, necrotic core, calcium, TCFA, or the like.

In a case where an ROI is determined based on NIRAF data, the ROI is determined based on the high NIRAF region. The NIRAF signal indicates the presence of high-risk plaques and/or thrombosis. A neighborhood average can be calculated to introduce the NIRAF region so that the NIRAF region also indicates the size of the plaque (plaque burden) or thrombosis. Also, the NIRAF region could be the highest NIRAF data in the pullback so that the ROI reflects the highest progressive region.

A defect region (shadow) is determined based on the guidewire shadow. The guidewire is used to navigate the MMOCT catheter to the coronary artery, however, the guidewire is made of non-transparent material, so the OCT and NIRAF images become shadows where the guidewire exists. The guidewire can be analyzed and detected by using the OCT data (the tissue surface (lumen) continuity, shadow area, strong reflection from the guidewire, etc.).

The following is an intravascular image processing according to the fourth embodiment. The method carries out steps of acquiring intravascular data of a portion of a lumen, determining an ROI based on characteristics of the acquired data, determining a position in a longitudinal position in a longitudinal direction for displaying an initial longitudinal view of the portion of the lumen based on the determined ROI, and displaying the initial longitudinal view based on the determined position and displaying a tomographic view of the portion of the lumen with selected tissue characteristics in a case where a user selects interested views.

The following is another method for intravascular image processing according to the fourth embodiment. The method carries out steps of acquiring intravascular data of a portion of a lumen, determining an ROI based on characteristics of the acquired data, determining a position in a longitudinal direction for displaying an initial longitudinal view of the portion of the lumen based on the determined ROI, and displaying one or more portions in the longitudinal view based on the determined position and displaying a tomographic view of the portion of the lumen.

The embodiments described above functionally implement intravascular MMOCT imaging and other intravascular imaging modalities including, for example, OCT, IVUS, fluorescence, NIRF, NIRAF, NIRS, hybrids or combinations thereof. The present disclosure is not limited to any particular configuration.

As described above, intravascular OCT uses an imaging catheter to acquire cross-sectional images of the target vessel. The OCT imaging catheter emits near-infrared light beams to the vessel tissue, and the backscattered light is measured so a detector can create a pixel for a specific site based on the produced light and dark patterns. The imaging catheter is rotated and pulled back by a motor when acquiring images and a sheath covers the imaging catheter. After scanning cross-sections successively at different transverse positions, a full 3D image of the vessel can be generated. A guidewire is normally present when intravascular OCT imaging takes place, so the generated images include the imaging catheter, the sheath, the guide wire, and the vessel lumen, as well as other items such as stent struts, side branches, or other lesions.

IVUS is a sound-based technique for visualizing arterial structure. IVUS may use a catheter with an ultrasound probe attached to the distal end of the catheter. The ultrasound probe emits a beam of ultrasound to the vessel tissue and receive the echo signal to acquire 2D cross-sectional images of coronary arteries. The catheter is pulled back through the target region to generate real-time 3D images and the images may be recorded on memory or storage for analysis. The ultrasound frequency may be around 20-40 MHz. There is a tradeoff between frequency and resolution in that the higher the frequency, the lower the penetration depth, and vice versa. The proximal end of the catheter can be attached to computerized equipment. IVUS determines the artery status including, for example, plaque buildup which leads to stenosis (narrowing) of the artery, the plaque volume within the wall of the artery and/or the degree of stenosis of the artery lumen.

NIRS is used to identify the chemical composition of unknown substances. Optical-based imaging using NIRF finds use in coronary artery-targeted intravascular imaging platform.

Fluorescence spectroscopy analyzes fluorescence, where a beam of light, such as ultraviolet light, excites electrons in molecules of certain compounds and causes them to emit light.

Intravascular fluorescence uses NIRAF or fluorescence generated by NIRF. Laser-induced fluorescence is used to stimulate fluorescence emission of particular vessel wall and plaque components or previously injected molecular agents. Imaging catheters contain an optical fiber to deliver and collect light to and from inner lumen of a person through semi-invasive interventions.

NIRS is a light-based imaging modality for detection of lipid-rich necrotic core in plaque.

Intravascular imaging acquires images from inside an artery and provides a variety of data or information associated with vessel size, lumen morphology.

Any form of imaging modality or combinations thereof is within the spirit and scope of the present disclosure.

A combination of NIRS with both OCT and IVUS can improve the accuracy of plaque characterization. NIRS includes one or more of a source, a detector, and a dispersive element, e.g. a prism, diffraction grating, or the like, to allow the intensity at different wavelengths to be recorded. Fourier transform NIR instruments using an interferometer can also be used for wavelengths above 1000 nm. Depending on the sample, the spectrum can be measured in either reflection or transmission.

A combination of OCT with NIRF and NIRAF molecular imaging can be configured to provide information about the functional state of corollary plaques, e.g. inflammation, macrophage activation, and other molecular processes. NIRAF is an endogenous signal, such as tissue autofluorescence, excited in the red (630-650 nm) and detected in the NIR. NIRAF is advantageous because it does not need exogenous agents and therefore, its path to clinical use is relatively straightforward.

Intravascular fluorescence is a catheter-based molecular imaging technique that uses NIRAF.

Intravascular imaging processing of an intravascular image according to the various embodiments described above enables determining an ROI based on characteristics of the acquired data, determining an angle (orientation) for displaying an initial longitudinal view of the portion of the lumen based on the determined ROI, and displaying the initial longitudinal view based on the determined angle and displaying a tomographic view of the portion of the lumen.

Features of the present disclosure facilitate ease of use, rapid exchange of the catheter with quick set up and pullback, and simplify interpretation of key vessel characteristics.

The units described throughout the present disclosure are exemplary and/or preferable modules for implementing processes described in the present disclosure. The term "unit", as used herein, may generally refer to firmware, software, hardware, or other component, such as circuitry or the like, or any combination thereof, that is used to effectuate a purpose. The modules can be hardware units (such as circuitry, firmware, a field programmable gate array, a digital signal processor, an application specific integrated circuit, or the like) and/or software modules (such as a computer readable program or the like). The modules for implementing the various steps are not described exhaustively above. However, where there is a step of performing a certain process, there may be a corresponding functional module or unit (implemented by hardware and/or software) for implementing the same process. Technical solutions by all combinations of steps described and units corresponding to these steps are included in the present disclosure.

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories, circuitry, or a combination thereof (e.g., central processing unit (CPU), micro processing unit (MPU), or the like), and may include a network of separate computers or separate processors to read out and execute the computer executable instructions. The computer executable instructions may be provided to the computerized configuration(s), for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. An intravascular image processing method comprising:
   acquiring intravascular data of a portion of a lumen along a longitudinal direction;
   determining an ROI (region of interest) based on characteristics of the acquired intravascular data, where the ROI comprises a defect region corresponding to a shadow of the acquired intravascular data;
   adjusting at least one of an orientation and angle of the intravascular data so the ROI appears and the defect region does not appear in the intravascular data;
   generating a longitudinal view of the portion of the lumen that is a cross sectional plane along the longitudinal direction;
   generating a tomographic view of the portion of the lumen that is a cross sectional plane perpendicular to the longitudinal direction; and
   automatically displaying, without user interaction, an initial display of the longitudinal view and the tomographic view of the portion of the lumen so the ROI appears and the defect region does not appear.

2. The method according to claim 1, wherein the characteristics are
   (a) fluorescence or tissue characteristics of the acquired intravascular data, or
   (b) shadows of the acquired intravascular data.

3. The method according to claim 1, wherein the method includes a record mode to acquire the intravascular data, a process mode to store the intravascular data, and a review mode to display the intravascular data.

4. The method according to claim 1, wherein the intravascular data is obtained by MMOCT (multi-modality optical coherence tomography).

5. The method according to claim 4, wherein the MMOCT includes one or more of OCT (optical coherence tomography), IVUS (intravascular ultrasound), NIRF (near infrared fluorescence), NIRAF (near infrared autofluorescence), and NIRS (near infrared spectroscopy).

6. The method according to claim 1, wherein the ROI includes one or more of
   (a) high fluorescence regions and tissue characteristics, or
   (b) guidewire characteristics with no fluorescence region.

7. The method according to claim 6, wherein the tissue characteristics include one or more of lipid, calcifications, bifurcation, thin-cap fibroatheroma, edge dissection, stent malapposition, stent underexpansion, thrombus, tissue protrusion, and stenosis.

8. The method according to claim 1, further comprising displaying a button on the display, and in response to a click on the display button, displaying the initial display.

9. The method according to claim 8, wherein the initial display comprises a cross-sectional longitudinal view or a three-dimensional half pipe cut longitudinal view of the portion of the lumen.

10. The method according to claim 1, further comprising determining the initial display of the portion of the lumen based on the ROI.

11. The method according to claim 1, wherein in a case there are multiple ROIs,
    selecting one of the multiple ROIs; and
    selecting another one of the multiple ROIs with a click on a display button.

12. The method according to claim 11, further comprising:
    simultaneously displaying the multiple ROIs.

13. The method according to claim 1, further comprising:
    displaying at least one of the orientation and angle on the tomographic view.

14. An intravascular image processing method comprising:
    acquiring intravascular data of a portion of a lumen along a longitudinal direction;
    determining an ROI (region of interest) based on characteristics of the acquired intravascular data, where the ROI comprises a defect region corresponding to a shadow of the acquired intravascular data;
    adjusting a position of the intravascular data in the longitudinal direction so the ROI appears and the defect region does not appear in the intravascular data;
    generating a longitudinal view of the portion of the lumen that is a cross sectional plane along the longitudinal direction;
    generating a tomographic view of the portion of the lumen that is a cross sectional plane perpendicular to the longitudinal direction; and
    automatically displaying, without user interaction, an initial display comprising the longitudinal view and the tomographic view of the portion of the lumen so the ROI appears and the defect region does not appear.

15. The method according to claim 14, wherein the characteristics are
    (a) fluorescence or tissue characteristics of the acquired intravascular data, or
    (b) shadows of the acquired intravascular data.

16. The method according to claim 14, wherein the method includes a record mode to acquire the intravascular data, a process mode to store the intravascular data, and a review mode to display the intravascular data.

17. The method according to claim 14, wherein the intravascular data is obtained by MMOCT (multi-modality optical coherence tomography).

18. The method according to claim 17, wherein the MMOCT includes one or more of OCT (optical coherence tomography), IVUS (intravascular ultrasound), NIRF (near infrared fluorescence), NIRAF (near infrared autofluorescence), and NIRS (near infrared spectroscopy).

19. The method according to claim 14, wherein the ROI includes one or more of
   (a) high fluorescence regions and tissue characteristics, or
   (b) guidewire characteristics with no fluorescence region.

20. The method according to claim 19, wherein the tissue characteristics include one or more of lipid, calcifications, bifurcation, thin-cap fibroatheroma, edge dissection, stent malapposition, stent underexpansion, thrombus, tissue protrusion, and stenosis.

21. The method according to claim 14, further comprising displaying a button on a display, and in response to a click on the display button, displaying the one or more portions.

22. The method according to claim 21, wherein the one or more portions is a cross-sectional longitudinal portion or a three-dimensional half pipe cut longitudinal portion.

23. The method according to claim 14, further comprising determining the initial display of the portion of the lumen based on the ROI.

24. The method according to claim 14, wherein in a case there are multiple ROIs,
   selecting one of the multiple ROIs; and
   selecting another one of the multiple ROIs with a click on a display button.

25. The method according to claim 24, further comprising:
   simultaneously displaying the multiple ROIs.

26. The method according to claim 14, further comprising:
   displaying the position on the initial display.

27. An intravascular image processing apparatus comprising:
   at least one processor configured to:
   acquire intravascular data of a portion of a lumen;
   determine an ROI (region of interest) based on characteristics of the acquired intravascular data, where the ROI comprises a defect region corresponding to a shadow of the acquired intravascular data;
   adjusting at least one of an orientation and angle of the intravascular data so the ROI appears and the defect region does not appear in the intravascular data;
   generate a longitudinal view of the portion of the lumen that is a cross sectional plane along the longitudinal direction;
   generate a tomographic view of the portion of the lumen that is a cross sectional plane perpendicular to the longitudinal direction; and
   automatically display, without user interaction, an initial display comprising the longitudinal view and the tomographic view of the portion of the lumen so the ROI appears and the defect region does not appear.

28. The intravascular image processing apparatus according to claim 27, wherein the characteristics are fluorescence or shadows of the acquired intravascular data.

29. The intravascular image processing apparatus according to claim 27, wherein the intravascular data is obtained by MMOCT (multi-modality optical coherence tomography).

30. The intravascular image processing apparatus according to claim 29, wherein the MMOCT includes one or more of OCT (optical coherence tomography), IVUS (intravascular ultrasound), NIRF (near infrared fluorescence), NIRAF (near infrared autofluorescence), and NIRS (near infrared spectroscopy).

31. The intravascular image processing apparatus according to claim 30, wherein the ROI includes one or more of
   (a) high fluorescence regions and tissue characteristics, or
   (b) guidewire characteristics with no fluorescence region.

32. The intravascular image processing apparatus according to claim 31, herein the tissue characteristics include one or more of lipid, calcifications, bifurcation, thin-cap fibroatheroma, edge dissection, stent malapposition, stent underexpansion, thrombus, tissue protrusion, and stenosis.

33. The intravascular image processing apparatus according to claim 31, further comprising determining the initial display based on the ROI.

34. The intravascular image processing apparatus according to claim 27, wherein in a case there are multiple ROIs, selecting one of the multiple MOIs; and
   moving to another ROI with a click on a display button.

35. A non-transitory storage medium storing a program for causing a computer to execute an intravascular image processing method for an image processing apparatus, the method comprising:
   acquiring intravascular data of a portion of a lumen along a longitudinal direction;
   determining an ROI (region of interest) based on characteristics of the acquired data, where the ROI comprises a defect region corresponding to a shadow of the acquired intravascular data;
   adjusting at least one of an orientation and angle of the intravascular data so the ROI appears and the defect region does not appear in the intravascular data;
   generating a longitudinal view of the portion of the lumen that is a cross sectional plane along the longitudinal direction;
   generating a tomographic view of the portion of the lumen that is a cross sectional plane perpendicular to the longitudinal direction; and
   automatically displaying, without user interaction, an initial display comprising the longitudinal view and the tomographic view of the portion of the lumen so the ROI appears and the defect region does not appear.

\* \* \* \* \*